United States Patent
Löscher et al.

(10) Patent No.: US 12,029,757 B2
(45) Date of Patent: *Jul. 9, 2024

(54) LIPID BARRIER REPAIR

(71) Applicant: DERMALIQ THERAPEUTICS, INC., Wilmington, DE (US)

(72) Inventors: Frank Löscher, Schriesheim (DE); Ralf Grillenberger, Nuremberg (DE); Chiara Silvana Leo, Heidelberg (DE); Markus Beier, Weinheim (DE)

(73) Assignee: DERMALIQ THERAPEUTICS, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/279,067

(22) PCT Filed: Sep. 20, 2019

(86) PCT No.: PCT/EP2019/075345
§ 371 (c)(1),
(2) Date: Mar. 23, 2021

(87) PCT Pub. No.: WO2020/064549
PCT Pub. Date: Apr. 2, 2020

(65) Prior Publication Data
US 2022/0079980 A1    Mar. 17, 2022

(30) Foreign Application Priority Data

Sep. 27, 2018  (EP) .................................. 18197200

(51) Int. Cl.
| | | |
|---|---|---|
| *A61K 9/06* | (2006.01) | |
| *A61K 31/07* | (2006.01) | |
| *A61K 31/593* | (2006.01) | |
| *A61K 33/18* | (2006.01) | |
| *A61K 47/06* | (2006.01) | |
| *A61K 47/10* | (2017.01) | |
| *A61K 47/44* | (2017.01) | |

(52) U.S. Cl.
CPC ................ *A61K 33/18* (2013.01); *A61K 9/06* (2013.01); *A61K 31/07* (2013.01); *A61K 31/593* (2013.01); *A61K 47/06* (2013.01); *A61K 47/10* (2013.01); *A61K 47/44* (2013.01)

(58) Field of Classification Search
CPC .......... A61K 33/18; A61K 9/06; A61K 31/07; A61K 31/593; A61K 47/06; A61K 47/10; A61K 47/44; A61K 8/0216; A61K 8/31; A61K 8/342; A61K 8/37; A61K 8/375; A61K 8/70; A61K 8/922; A61K 8/925; A61K 8/927; A61K 9/0014; A61K 31/02; A61K 8/92; A61K 31/573; A61P 17/00; A61P 17/04; A61P 17/06; A61P 17/10; A61Q 19/007; A61Q 19/08; A61Q 19/00
See application file for complete search history.

(56) References Cited

U.S. PATENT DOCUMENTS

| | | |
|---|---|---|
| 2,616,927 A | 11/1952 | Kauck et al. |
| 5,077,036 A | 12/1991 | Long |
| 5,152,997 A | 10/1992 | Elbert et al. |
| 5,254,338 A | 10/1993 | Sakai et al. |
| 5,326,566 A | 7/1994 | Parab |
| 5,340,567 A | 8/1994 | Cole et al. |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers et al. |
| 5,904,933 A | 5/1999 | Riess et al. |
| 5,980,936 A | 11/1999 | Krafft et al. |
| 6,042,845 A | 3/2000 | Sun et al. |
| 6,060,085 A | 5/2000 | Osborne |
| 6,113,919 A | 9/2000 | Reiss et al. |
| 6,159,977 A | 12/2000 | Reeves |
| 6,224,887 B1 | 5/2001 | Samour et al. |
| 6,262,126 B1 | 7/2001 | Meinert |
| 6,391,879 B1 | 5/2002 | Reeves |
| 6,486,212 B2 | 11/2002 | Meinert |
| 6,489,367 B1 | 12/2002 | Meinert |
| 8,029,977 B2 | 10/2011 | Meinert et al. |
| 8,470,873 B2 | 6/2013 | Chen |
| 8,614,178 B2 | 12/2013 | Theisinger et al. |
| 8,759,281 B2 | 6/2014 | Bonnet et al. |
| 8,986,738 B2 | 3/2015 | Meinert |
| 9,186,305 B1 | 11/2015 | Suzuki |
| 9,241,900 B2 | 1/2016 | Wilson |

(Continued)

FOREIGN PATENT DOCUMENTS

| | | |
|---|---|---|
| CN | 106176937 | 12/2016 |
| EP | 0 433 086 | 12/1990 |

(Continued)

OTHER PUBLICATIONS

English translation of JPS62249913 retrieved from Espacenet on Nov. 10, 2022. (Year: 1987).*
Bardin et al., "Long-Range Nanometer-Scale Organization of Semifluorinated Alkane Monolayers at the Air/Water Interface," Langmuir, 2011, 27, 13497-13505.
Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.

(Continued)

*Primary Examiner* — Jessica Worsham
(74) *Attorney, Agent, or Firm* — Hoxie & Associates LLC (57) ABSTRACT

The present disclosure is in the field of ointments which can be useful for the treatment of diseases or conditions associated with lipid barrier damage of the skin. The ointment comprises a semifluorinated alkane and a solid thickening agent, e.g., a wax, a triglyceride, cetyl alcohol, cetyl palmitate, or tetradecanol.

21 Claims, 1 Drawing Sheet

(56) References Cited

U.S. PATENT DOCUMENTS

| | | | |
|---|---|---|---|
| 9,308,262 B2 | 4/2016 | Günther et al. |
| 9,757,459 B2 | 9/2017 | Günther et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 10,130,707 B2 | 11/2018 | Günther et al. |
| 10,273,298 B2 | 4/2019 | Günther et al. |
| 10,449,164 B2 | 10/2019 | Günther et al. |
| 10,507,132 B2 | 12/2019 | Graf et al. |
| 10,682,315 B2 | 6/2020 | Scherer et al. |
| 10,813,999 B2 | 10/2020 | Günther et al. |
| 11,154,513 B2 | 10/2021 | Scherer et al. |
| 11,273,174 B2 | 3/2022 | Löscher et al. |
| 2002/0004063 A1 | 1/2002 | Zhang |
| 2002/0128527 A1 | 9/2002 | Meinert |
| 2003/0027833 A1 | 2/2003 | Cleary et al. |
| 2003/0170194 A1 | 9/2003 | Piotrowiak |
| 2004/0101551 A1 | 5/2004 | Selzer |
| 2004/0265362 A1 | 12/2004 | Susilo |
| 2005/0075407 A1 | 4/2005 | Tamarkin et al. |
| 2005/0079210 A1 | 4/2005 | Gupta |
| 2005/0084553 A1 | 4/2005 | Moon et al. |
| 2005/0175541 A1 | 8/2005 | Lanza et al. |
| 2005/0288196 A1 | 12/2005 | Horn |
| 2006/0078577 A1 | 4/2006 | Dechow |
| 2006/0153905 A1 | 7/2006 | Carrara et al. |
| 2006/0204458 A1 | 9/2006 | Holloway et al. |
| 2008/0019926 A1 | 1/2008 | Krafft et al. |
| 2008/0207537 A1 | 8/2008 | Turner et al. |
| 2008/0254106 A1 | 10/2008 | Bell |
| 2008/0260656 A1 | 10/2008 | Mallard |
| 2009/0104243 A1 | 4/2009 | Utkhede et al. |
| 2009/0169601 A1 | 7/2009 | Koch et al. |
| 2009/0226875 A1 | 9/2009 | Meinert et al. |
| 2010/0008996 A1 | 1/2010 | Meinert |
| 2010/0305081 A1 | 12/2010 | Dechow |
| 2011/0269704 A1 | 11/2011 | Seigfried |
| 2012/0100183 A1 | 4/2012 | Schlessinger et al. |
| 2012/0219640 A1 | 8/2012 | Wright |
| 2012/0238639 A1 | 9/2012 | Theisinger et al. |
| 2013/0011484 A1 | 1/2013 | Bevier |
| 2013/0084250 A1 | 4/2013 | Hagedorn et al. |
| 2013/0266652 A1 | 10/2013 | Theisinger et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0000941 A1 | 1/2016 | Thorsten et al. |
| 2016/0101178 A1 | 4/2016 | Wilson |
| 2016/0159902 A1 | 6/2016 | Günther et al. |
| 2017/0087100 A1 | 3/2017 | Scherer et al. |
| 2017/0087101 A1 | 3/2017 | Scherer et al. |
| 2017/0143832 A1 | 5/2017 | Günther et al. |
| 2017/0182060 A1 | 6/2017 | Wiedersberg et al. |
| 2018/0021434 A1 | 1/2018 | Günther et al. |
| 2019/0125658 A1 | 5/2019 | Ficko |
| 2020/0129543 A1 | 4/2020 | Loscher et al. |
| 2020/0246463 A1 | 8/2020 | Günther et al. |
| 2020/0338015 A1 | 10/2020 | Scherer et al. |
| 2021/0069014 A1 | 3/2021 | Löscher et al. |
| 2021/0100904 A1 | 4/2021 | Günther et al. |
| 2021/0308024 A1 | 10/2021 | Löscher et al. |
| 2022/0031844 A1 | 2/2022 | Mauden et al. |
| 2022/0152096 A1 | 5/2022 | Löscher et al. |
| 2022/0218828 A1 | 7/2022 | Günther et al. |

FOREIGN PATENT DOCUMENTS

| | | | |
|---|---|---|---|
| EP | 0 670 159 | 9/1995 | |
| EP | 1 152 749 | 4/2006 | |
| JP | S5721312 A | 2/1982 | |
| JP | H0764702 B2 | 7/1995 | |
| RU | 2 111 738 C1 | 5/1998 | |
| WO | WO 1998/005301 | 12/1998 | |
| WO | WO 2012/007776 | 1/2012 | |
| WO | WO-2012160179 A2 * | 11/2012 | ............. A61K 31/07 |
| WO | WO-2013188273 A1 * | 12/2013 | ......... A61K 31/4439 |
| WO | WO 2017/210777 | 12/2017 | |
| WO | WO 2018/193093 | 10/2018 | |
| WO | WO 2021/156493 A1 | 8/2021 | |

OTHER PUBLICATIONS

Broniatowski, M. et al., "Langmuir Monolayers Characteristic of (Perfluorodecyl)-Alkanes," Journal of Physical Chemistry B, 2004, 108, 13403-13411.

Chuanfu, Y., "Pharmaceutics," People's Medical Publishing House, 1986.

Chemical Book, 5-Fluorouracil, available at <http://www.chemicalbook.com/ChemicalProductProperty_EN_CB8162744.htm>, accessed Mar. 7, 2014, 1 page.

CN106176937A, Liu Yipeng, "Eczema-acne ointment," Dec. 7, 2016, English language machine translation of abstract, Espacenet, date obtained: Apr. 30, 2021, 1 page <https://worldwide.espacenet.com/patent/search/family/058089634/publication/CN106176937A?q=CN106176937A>.

Costa Gomes et al., "Solubility of dioxygen in seven fluorinated liquids," Journal of Fluorine Chemistry, 2004, 125, 1325-1329.

Dembinski, R. et al., "Semi-fluorinated Alkanes as Carriers for Drug Targeting in Acute Respiratory Failure," Experimental Lung Research, 2010, 36, 499-507.

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, 2004.

Dias et al., "Solubility of oxygen in liquid perfluorocarbons," Fluid Phase Equilibria, 2004, 222-223:325-330.

Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).

Elkeeb, R. et al., "Transungual Drug Delivery: Current Status," International Journal of Pharmaceutics, 2010, 384, 1-8.

English-language machine translation of EP0670159 (A1) issued in U.S. Appl. No. 14/122,025, filed Apr. 1, 2015, 10 pages.

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gerdenitsch, "Emulsions—established and promising drug carriers for parenteral administration," retrieved from Internet, date accessed: Jun. 20, 2016, URL: <http://ipimediaworld.com/wp-content/uploads/2012/05/Pages-from-IPI-Volume-2-Issue-1-11.pdf>.

Griffin, W., "Classification of Surface-Active Agents by 'HLB'," Journal of the Society of Cosmetic Chemists, 1949, 1, 311-326.

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

Holm, R. et al., "A novel excipient, 1-perfluorohexyloctane shows limited utility for the oral delivery of poorly water-soluble drugs," European Journal of Pharmaceutical Sciences, 2011, 42: 416-422.

International Preliminary Report on Patentability dated Mar. 30, 2021, for International Application No. PCT/EP2019/075345, 9 pages.

(56) References Cited

OTHER PUBLICATIONS

International Search Report and Written Opinion for International Application No. PCT/EP2019/075345 mailed Apr. 2, 2020, 14 pages.
JPH0764702B2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.
JPS5721312A, Green Cross Corp, "Breathable Ointment," Apr. 2, 1982, English language machine translation of abstract, Espacenet, date obtained: Apr. 30, 2021, 1 page <https://worldwide.espacenet.com/patent/search/family/014132731/publication/JPS5721312A?q=JPS5721312A>.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, N., et al., "Influence on Membrane-Mediated Cell Activation by Vesicles of Silicone Oil or Perfluorohexyloctane," Graefe's Archive for Clinical and Experimental Ophthalmology, 2005, 243, 345-358.
Mantle et al., "Adverse and beneficial effects of plant extracts on skin and skin disorders," Adverse Drug Reaction and Toxicological Reviews, 2001, 20(2): 89-103.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10 (3), 189-197.
Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Murdan, S., "Enhancing the Nail Permeability of Topically Applied Drugs," Expert Opinion on Drug Delivery, 2008, 5 (11), 1267-1282.
Plassmann, M. et al., "Trace Analytical Methods for Semifluorinated n-Alkanes in Snow, Soil, and Air," Analytical Chemistry, 2010, 82(11), 4551-4557.
Plassmann, M. et al., "Theoretical and Experimental Simulation of the Fate of Semifluorinated n-Alkanes During Snowmelt," Environmental Science & Technology, 2010, 44 (17), 6692-6697.
Rosca-Casian, O. et al., "Antifungal Activity of Aloe vera Leaves," Fitoterapia, 2007, 28, 219-222.
RU2111738C1, Aktsionerone Obshchestvo Nizar, "Product to Enhance Sun-Protecting Activity of Photo-Protecting Agents," May 27, 1998, English language machine translation of abstract, Espacenet, date obtained: Apr. 30, 2021, 1 page <https://worldwide.espacenet.com/patent/search/family/020182059/publication/RU2111738C1?q=RU2111738C1>.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Stevenson, C., "Characterization of Protein and Peptide Stability and Solubility in Non-Aqueous Solvents," Current Pharmaceutical Biotechnology, 2000, 1, 165-182.
Thomas et al., "The therapeutic uses of topical vitamin A acid," Journal of the American Academy of Dermatology, 1981, 4(5): 505-513.
Ujiie et al., "Successful Treatment of Nail Lichen Planus with Topical Tacrolimus", Department of Dermatology, Hokkaido University Graduate School of Medicine, 2009.
Wong, D. et al., "Perfluorocarbons and Semifluorinated Alkanes," Seminars in Ophthalmology, 2000, 15 (1), 25-35.
Xiangqun, J. et al., "Professional Knowledge on Pharmaceutical Field," Military Medical Science Press, 2009, vol. 2.
Yaoxue Zhuanye Zhishi II (Editor: Jin Xiangqun), Military Medical Science Press, 1 $^{st}$ Printing of $2^{nd}$ Edition, Mar. 2009, p. 158.
Yaoxue Zhuanye Zhishi II (Editor: Jin Xiangqun), Military Medical Science Press, 1 $^{st}$ Printing of $2^{nd}$ Edition, Mar. 2009, p. 158, 3 pages (English Machine Translation).
Zakeri et al., "Topical calcipotriol therapy in nail psoriasis", A study of 24 cases, Dermatology Online Journal, 11(3):5; 2005.
Zhang et al., "Surface micelles of semifluorinated alkanes in Langmuir-Blodgett monolayers," Phys. Chem. Chem. Phys., 2004, 6, 1566-1569.
Blume-Peytavi et al., "A Randomized Double-blind Placebo-controlled Pilot Study to Assess the Efficacy of a 24-week Topical Treatment by Latanoprost 0.1% on Hair Growth and Pigmentation in Healthy Volunteers with Androgenetic Alopecia," J Am Acad Dermatol, 2012, 66(5): 794-800.
"Clascoterone (Winlevi®)," Chemical Abstracts, CAS Registry No. 19608-29-8, retrieved from the Internet, date accessed: Feb. 9, 2022, 3 pages URL: <https://www.chemicalbook.com/CASEN_19608-29-8.htm>.
Xalatan, Latanoprost Ophthalmic Solution, 50 μg/mL Prostaglandin $F_{2\alpha}$ analogue, Product Monograph, Jul. 21, 2014, 30 pages.
Steve Mason, Alberta Dairy Management, "Facts about Fats" (undated) available at http://www.agromedia.ca/ADM_Articles/content/fatfacts.pdf (last accessed Nov. 22, 2023).
Lipid, Encyclopaedia Brittanica, Inc. (Eds.), Nov. 7, 2023, available at https://www.britannica.com/print/article/342808 (last accessed Nov. 22, 2023).

* cited by examiner

LIPID BARRIER REPAIR

CROSS-REFERENCE TO RELATED APPLICATIONS

This application is a U.S. National Stage application under 35 U.S.C. § 371 of International Application No. PCT/EP2019/075345, filed on Sep. 20, 2019, which claims priority to and the benefit of European Applications No. 18197200.1, filed on Sep. 27, 2018, the contents of which are hereby incorporated by reference in its entirety.

The present invention relates to ointments comprising semifluorinated alkanes. The ointments of the present invention may be used as an ointment base for the preparation of further pharmaceutical or cosmetic compositions. In particular, the ointments of the present invention may be used for the treatment of skin diseases and conditions related to the lipid barrier damage of the skin such as psoriasis, dermatitis, acne and the symptoms related thereof.

BACKGROUND ART

Ointments are semisolid preparations for external application to the body. Therapeutically, ointments function as protectives and emollients for the skin, but they are used primarily as vehicles or bases for the topical application of medicinal substances. Ideally, an ointment base should be compatible with the skin, stable, permanent, smooth and pliable, non-irritating, non-sensitising, inert and readily able to release its incorporated medication. Ointments are classified best according to their composition in oleaginous, emulsifiable, emulsion bases and water soluble.

The oleaginous ointment bases include oils of vegetable origins, fat from animals and semisolid hydrocarbons obtained from petroleum. The vegetable oils and the animal fats have two marked disadvantages as ointment bases: their water absorbing capacity is low and they have a tendency to become rancid. The hydrocarbon bases comprise a group of substances with a wide range of melting points. They are stable, bland and chemically inert and will mix with virtually any chemical substance. Examples of oleaginous ointments comprise white ointments (white wax and white petrolatum), yellow ointment (yellow wax and petrolatum), cetyl esters wax, petrolatum (a purified mixture of semisolid hydrocarbons obtained from petroleum).

Absorbent ointment bases, sometimes called emulsifiable ointment bases, are generally anhydrous substances that have the property of absorbing (emulsifying) considerable amounts of water and still retaining their ointment like consistency. Examples are lanolin anhydrous, hydrophilic petrolatum.

The emulsion ointment bases are actually semisolid emulsions, divided in ointment base oil in water emulsions and ointment base water in oil emulsions.

Water soluble ointment bases include bases prepared from the higher ethylene glycol polymers, marketed under the trademark Carbowax™. (Remington, "The Science and practice of pharmacy", pages 1076-1080).

Oleaginous bases are occlusive and protect the skin from the air. They are hydrophobic, so they do not wash off with water and they feel greasy to the touch. Oleaginous bases are used mainly for their lubricating effect because they do not allow moisture to escape from the skin, do not dry out and remain on the skin for a long time. Vaseline petroleum jelly is an example of an oleaginous base.

The mammalian skin is a highly complex organ with a variety of advanced functions, one of the most important being to act as a barrier to excessive water loss, and xenobiotic and microbial assaults. A properly functioning barrier is essential for a healthy skin, but it also constitutes a challenge for the development of pharmaceutical and active cosmetic formulations, in which penetration of active compounds is crucial.

Crucial for this skin barrier function is the lipid matrix in the outermost layer of the skin, the stratum corneum (SC). Two of its functions are (1) to prevent excessive water loss through the epidermis and (2) to avoid that compounds from the environment permeate into the viable epidermal and dermal layers and thereby provoke an immune response. The composition of the SC lipid matrix is dominated by three lipid classes: cholesterol, free fatty acids and ceramides. These lipids adopt a highly ordered, 3-dimensional structure of stacked densely packed lipid layers (lipid lamellae): the lateral and lamellar lipid organization.

Disturbances of skin barrier function occur in several skin diseases, e.g. atopic dermatitis (AD), irritant/allergic contact dermatitis (ICD, ACD). Skin barrier damage triggers the production of cytokines that stimulate lipogenesis which may also cause inflammatory processes.

Dermatitis refers to the inflammation of the skin, characterized by itchiness, rash and red skin. In cases of short duration, there may be small blisters, while in long-term cases the skin may become thickened. Dermatitis is a group of skin conditions that includes atopic dermatitis, allergic contact dermatitis and irritant contact dermatitis. The exact cause of dermatitis is often unclear. Cases may involve a combination of irritation, allergy and poor venous return.

Irritant contact dermatitis is the result of a non-specific cellular damage to the skin caused either by physical factors, such as mechanical friction or cold, or more commonly by chemicals. It often occurs on the hands of people who frequently get them wet. Allergic contact dermatitis occurs upon exposure to an allergen, causing a hypersensitivity reaction in the skin.

The most frequent sign of environmental induced dermatitis is dry skin (xerosis). Dryness is usually associated with impaired barrier function, although the clinical appearance of dryness can be confined to changes in the outermost structure of the stratum corneum with an intact permeability barrier beneath. Moisturizers usually promote normalisation of the skin (Am. J. Clin. Dermatol. 2003; 4(11); 771-788).

Although the symptoms of atopic dermatitis vary from person to person, the most common symptoms are dry, itchy, red skin. Typical affected skin areas include the folds of the arms, the back of the knees, wrists, face and hands.

Treatment of atopic dermatitis is typically with moisturizers and steroid creams. The steroid creams should generally be of mid- to high strength and used for less than two weeks at a time as side effects can occur. Antibiotics may be required if there are signs of skin infection.

Psoriasis is an immune-mediated disease which affects the skin and joints. It commonly causes red scaly patches to appear on the skin. The scaly patches caused by psoriasis are often called psoriasis plaques or lesions. Psoriasis plaques are areas of excessive skin cell production and inflammation. Skin rapidly accumulates at these sites and sometimes takes a silvery-white appearance. Plaques frequently occur on the skin of the elbows and knees, but can affect any area including the scalp and genitals.

Acne, also known as acne vulgaris, is a long-term skin disease that occurs when hair follicles are clogged with dead skin cells and oil from the skin. It is characterized by blackheads or whiteheads, pimples, oily skin, and possible scarring. It primarily affects areas of the skin with a relatively high number of oil glands, including the face, upper part of the chest, and back.

Emollients and moisturizing creams are used to break the dry skin cycle and to maintain the smoothness of the skin. The term 'moisturizer' is often used synonymously with emollient, but moisturizers often contain humectants in order to hydrate the stratum corneum. Moisturizers have multiple functions apart from moistening the skin. Similar to other actives, the efficacy is likely to depend on the dosage, where compliance is a great challenge faced in the management of skin diseases. Strong odour from ingredients and greasy compositions may be disagreeable to the patients. Furthermore, low pH and sensory reactions, from lactic acid and urea for example, may reduce patient acceptance. Once applied to the skin, the ingredients can stay on the surface, be absorbed into the skin, be metabolized, or disappear from the surface by evaporation, sloughing off, or by contact with other materials.

By definition, moisturizers contain occlusive ingredients, such as petrolatum or lanolin, which coat the surface of the skin with a water-repellent lipid layer that impedes the bidirectional movement of water across the skin. Because they block water loss out of the skin, these agents can temporarily ameliorate the xerosis that is characteristic of diseases related to lipid barrier damage and age-associated eczematous disorders. Moreover, by improving the hydration of the stratum corneum, they can dampen inflammation.

Ointments are usually very moisturizing, and good for dry skin. They have a low risk of sensitization due to having few ingredients beyond the base oil or fat, and low irritation risk. They are often disliked by patients due to greasiness.

SUMMARY OF THE INVENTION

The objective of the present invention is to provide an ointment which is useful for therapeutic and cosmetic applications and which may be used to treat or prevent skin disorders related to the lipid barrier damage of the skin, such as dermatitis, psoriasis, acne. The objective of the present invention is attained by the claims.

The ointment composition of the present invention has the advantage of being less viscous than other water free ointments, like oleaginous ointments, therefore resulting in an ointment which penetrates in the stratum corneum quickly and completely, without leaving any greasy residues on the skin and on the textiles/clothing and without clogging the sebaceous glands. Further, the ointment composition of the present invention gives a pleasant silky feeling during and after application on the skin. Another advantage of the ointment of the present invention is that it can transport oxygen to the skin in amount higher than other ointments. Oxygenation of the skin is relevant for a healthy skin.

DETAILED DESCRIPTION OF THE INVENTION

Figure 1:
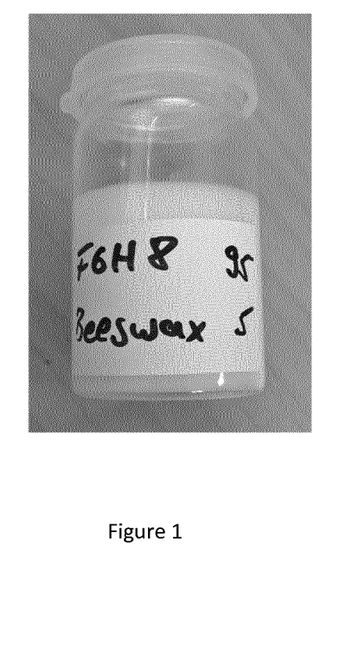
FIG. 1 represents an ointment obtained according to the procedure described in the Examples and comprising F6H8 at a concentration of 95 percent by weight and beeswax at a concentration of 5 percent by weight based on the total weight of the composition.
Figure 2:
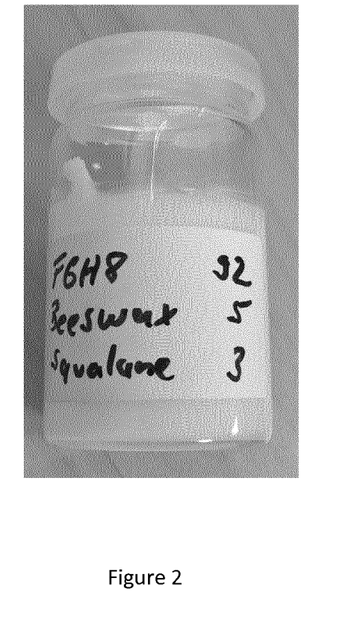
FIG. 2 represents an ointment obtained according to the procedure described in the Examples and comprising F6H8 at a concentration of 92 percent by weight, beeswax at a concentration of 5 percent by weight and squalane at a concentration of 3 percent by weight based on the total weight of the composition.

In a first aspect the present invention provides a composition in form of an ointment comprising a semifluorinated alkane, a solid thickening agent and optionally an excipient.

An ointment is a homogeneous, semi-solid preparation, that is intended for external application to the skin or mucous membranes.

Semifluorinated alkanes are linear or branched alkanes, some of whose hydrogen atoms have been replaced by fluorine. The term "semifluorinated alkane", also referred to as "SFA" throughout this document, as used herein refers to a linear or branched compound composed of at least one perfluorinated segment (F-segment) and at least one non-fluorinated hydrocarbon segment (H-segment). Preferably, the semifluorinated alkane is a linear or branched compound composed of one perfluorinated segment (F-segment) and one non-fluorinated hydrocarbon segment (H-segment). Preferably, said semifluorinated alkane is a compound that exists in a liquid state within the temperature range of 4° to 40° C. In one embodiment, the perfluorinated segment and/or the hydrocarbon segment of the said SFA optionally comprises or consists of a cyclic hydrocarbon segment, or optionally said SFA comprises an unsaturated moiety within the hydrocarbon segment.

It is preferred that the F- and the H-segment of the linear or branched semifluorinated alkane comprise, independently from one another, 2 to 10 carbon atoms.

According to a preferred embodiment of the present invention, the semifluorinated alkane is a linear compound of the formula (I) $CF_3(CF_2)_n(CH_2)_mCH_3$, wherein n and m are integers independently selected from each other from the range of 2 to 10.

According to another nomenclature, the linear semifluorinated alkane may be referred to as FnHm, wherein F means the perfluorinated hydrocarbon segment, H means the non-fluorinated hydrocarbon segment and n, m is the number of carbon atoms of the respective segment. For example, F4H5 is used for 1-perfluorobutyl-pentane. In a preferred embodiment of the present invention, the semifluorinated alkane is a semifluorinated alkane of formula (I) $CF_3(CF_2)_n(CH_2)_mCH_3$ wherein n is selected from 3 to 5 and m is selected from 4 to 9. More preferred is a semifluorinated alkane selected from the group consisting of F4H5, F4H6, F4H8, F4H10, F6H8, F6H10. Most preferred is a semifluorinated alkane selected from F4H8, F6H8 and F6H10.

Preferably the composition of the present invention comprises a semifluorinated alkane at a concentration of from 50 to 97 percent by weight, preferably from 70 to 97 percent by weight, more preferably from 80 to 97 percent by weight based on the total weight of the composition. Most preferably, the semifluorinated alkane is present at a concentration of from 85 to 95 percent by weight based on the total weight of the composition.

In a preferred embodiment, the semifluorinated alkane is present at a concentration of at least 50 percent, preferably at least 70 percent, more preferably at least 80 percent, most preferably at least 85 percent by weight based on the total weight of the composition. In a more preferred embodiment, the semifluorinated alkane is present at a concentration of up to 95 percent by weight based on the total weight of the composition.

In the present invention a solid thickening agent is comprised in the composition in form of an ointment. Solid thickeners which may be employed in the present invention comprise plant waxes, animal waxes, petroleum derived waxes, solid and semisolid triglycerides, $C_{12-24}$ fatty acids, $C_{8-18}$ glycerides, fatty alcohols, fatty alcohols derivatives and any combinations thereof. Non limiting examples of waxes are bees wax, lanolin wax (wool wax), lanolin wax derivatives, carnauba wax, candelilla wax, castor wax, rice bran wax, spermaceti wax, bran wax, montan wax, kapok wax, bay berry wax, shellac wax, sugar cane wax, paraffin wax, ceresin wax.

In a preferred embodiment, the solid thickening agent is selected from plant waxes, animal waxes, petroleum derived waxes, solid and semisolid triglycerides, cetyl alcohol, cetyl palmitate 15, tetradecanol and any combinations thereof. In a more preferred embodiment, the solid thickening agent is one or more selected from beeswax, carnauba wax, cetyl alcohol, tetradecanol, petroleum derived waxes, paraffin wax, cetyl palmitate 15, solid and semisolid triglycerides. More preferably, the solid thickening agent is selected from beeswax, solid and semisolid triglycerides, petroleum derived wax, such as vaseline, cetyl alcohol, tetradecanol, cetyl palmitate 15, paraffin wax and any combinations thereof.

The solid thickening agent may be comprised at a concentration of from 3 to 50 percent by weight, preferably at a concentration of from 3 to 30 percent by weight, more preferably from 3 to 20 percent by weight, most preferably from 3 to 11 percent by weight based on the total weight of the composition.

Preferably, the composition of the present invention does not comprise any preservative.

The composition of the present invention may further comprise an active ingredient. Preferably, the active ingredient is one selected from antiseptics, corticosteroids, antibiotics, calcineurin inhibitors, anaesthetics, retinoids, vitamin D analogues, immunosuppressants, prostaglandins analogues, capsaicinoids, avermectins. In a preferred embodiment, the active ingredient may be one selected from molecular iodine, prostaglandin analogues, ivermectin, capsaicin, cyclosporin, tacrolimus, corticosteroids, calcineurin inhibitors, retinoids, vitamin D analogues. In a most preferred embodiment, the active ingredient is one selected from molecular iodine, cyclosporin, latanoprost, capsaicin and ivermectin.

The active ingredient may be comprised at a concentration of up to 10 percent by weight with respect to the total weight of the composition, preferably of up to 5 percent by weight with respect to the total weight of the composition. In a preferred embodiment, the active ingredient is present at a concentration of from 0.05 to 10 percent by weight, preferably of from 0.05 to 5 percent by weight with respect to the total weight of the composition.

Optionally, the composition of the present invention may further comprise an excipient such as a cosolvent or an oily material, such as those useful in the preparation of ointments. An excipient may be present at a concentration of up to 45 percent by weight, based on the total weight of the composition. In a preferred embodiment, an excipient is present at a concentration of up to 25 percent by weight, preferably up to 10 percent by weight, more preferably up to 6 percent by weight based on the total weight of the composition. More preferably an excipient is present at a concentration of from 1 to 45 percent by weight, most preferably of from 1 to 25 percent by weight, even most preferably of from 1 to 10 percent by weight based on the total weight of the composition.

Examples of cosolvents which may be included in the composition of the present invention are isopropanol, ethanol, liquid medium chain triglycerides, N-methyl-2-pyrrolidone, diethylene glycol monomethylether, diethylene glycol monoethylether, ethyl acetate, ethyl oleate, octyldodecanol, diethyl sebacate. Preferably, the cosolvent is selected from isopropanol, ethanol, liquid medium chain triglycerides, diethylene glycol monoethylether, diethyl sebacate.

A cosolvent may be present at a concentration of from 0.5 to 10 percent by weight, preferably 0.5 to 5 percent by weight, based on the total weight of the composition.

Examples of oily materials are squalane, squalene, thymol, essential oils, liquid triglycerides, silicone oils like cyclomethicone and dimethicone, mineral oils, emollient vegetable oils such as olive, coconut, jojoba, sesame, avocado, sunflower, safflower, borage, corn, and sea buckthorn oil. In a preferred embodiment, the composition of the present invention comprises an oily material selected from squalane, squalene, silicone oils, mineral oils, essential oils, liquid triglycerides, vegetable oils.

An oily material may be present at a concentration of from 0.1 to 25 percent by weight, preferably of from 0.1 to 10 percent by weight based on the total weight of the composition.

Emollients like isopropyl myristate and isopropyl palmitate can be included in the composition of the present invention.

Water can also be present in the composition of the present invention, however preferably in small or trace amounts of up to 1.0 percent by weight or even up to 0.1 percent by weight based on the total weight of the composition. In a preferred embodiment, the composition of the present invention is essentially free of water, whereas the residual water may be attributed to the potential water content of the chosen active ingredient. The term 'essentially' as used herein means if present then in trace or residual amounts such as to confer no technical advantage or relevance in respect of the object of the invention. In a more preferred embodiment, the composition in the form of an ointment is a water free ointment.

All the embodiments and preferred embodiments relating to the composition of the first aspect of the invention as described above apply also to any of the following aspects of the present invention.

In a second aspect of the present invention, the composition according to the first aspect of the invention may be used as a medicament, in particular it may be used in the prevention or treatment of a disease or condition associated with the lipid barrier damage of the skin. Examples of diseases associated with the lipid barrier damage are dermatitis, psoriasis, acne. In a preferred embodiment, the lipid barrier damage related disease is one selected from irritant contact dermatitis, allergic contact dermatitis, atopic dermatitis, psoriasis, acne. Preferably the lipid barrier damage related disease is dermatitis or psoriasis, more preferably dermatitis. Conditions associated with lipid barrier damage of the skin may be dry skin, aged skin, itchiness.

In a third aspect, the present invention provides for a method of treatment of a disease or condition associated with the lipid barrier damage of the skin comprising administering the composition according to the first aspect of the invention topically to the skin of a subject suffering from a disease or condition associated with lipid barrier damage of the skin. The lipid barrier damage related disease may be one selected from dermatitis, psoriasis, acne, preferably one selected from irritant contact dermatitis, allergic contact dermatitis, atopic dermatitis, psoriasis, acne. In a preferred embodiment the lipid barrier damage related disease is dermatitis or psoriasis, more preferably dermatitis. Conditions associated with lipid barrier damage of the skin may be dry skin, aged skin, itchiness.

In a fourth aspect, the present invention provides for the use of the composition of the first aspect of the invention in a method of treating of a disease or condition associated with the lipid barrier damage of the skin.

In a fifth aspect, the present invention provides for the use of the composition of the first aspect of the invention for the manufacture of a medicament for the treatment of a disease or condition associated with lipid barrier damage of the skin.

In a sixth aspect, the present disclosure provides a kit comprising a composition according to the first aspect of the invention and a container for holding the composition. The container can be for example a jar, a tube, a bottle, a dispenser or other types of containers suitable for holding the composition. The containers can have for example a pump and/or a squeeze mechanism.

The kit may include a package comprising the container in which the composition of the first aspect of the present invention is placed. In the package, instructions for use can be included.

In summary the present invention comprises the following items:
1. A composition in form of an ointment comprising:
   a) a semifluorinated alkane
   b) a solid thickening agent
   c) optionally an excipient
2. The composition according to item 1, wherein the composition further comprises an active ingredient.
3. The composition of any preceding items, wherein the semifluorinated alkane is of formula F(CF2)n(CH2)mH wherein n is an integer selected from 2 to 10 and m is an integer selected from 2 to 10.
4. The composition of item 3, wherein n is an integer selected from 4 to 6 and m is an integer selected from 5 to 10.
5. The composition of any preceding item, wherein the semifluorinated alkane is selected from 1-perfluorbutyl-pentane (F4H5), 1-perfluorbutyl-hexane (F4H6), 1-perfluorobutyl-octane (F4H8), 1-perfluorobutyl-decane (F4H10), 1-perfluorohexyl-octane (F6H8), 1-perfluorohexyl-decane (F6H10) and combinations thereof.
6. The composition of any preceding item, wherein the semifluorinated alkane is selected from 1-perfluorohexyl-octane (F6H8), 1-perfluorbutyl-pentane (F4H5), 1-perfluorohexyldecane (F6H10) and 1-perfluorobutyl-octane (F4H8), preferably selected from 1-perfluorohexyl-octane (F6H8) and 1-perfluorobutyl-octane (F4H8).
7. The composition of any preceding item, wherein the composition comprises a mixture of semifluorinated alkanes, preferably a mixture selected from a) F6H8 and F4H8, b) F4H8 and F6H10, c) F6H8 and F6H10.
8. The composition of any preceding item, wherein the composition comprises 50-98 wt % of a semifluorinated alkane based on the total weight of the composition.
9. The composition of any preceding item, wherein the composition comprises a semifluorinated alkane at a concentration of from 50-97 percent by weight, preferably 70-97 percent by weight, more preferably 80-97 percent by weight based on the total weight of the composition.
10. The composition of any preceding item, wherein the composition comprises 85-95 percent by weight of a semifluorinated alkane based on the total weight of the composition.
11. The composition of any preceding item, wherein the composition comprises at least 70 wt % of a semifluorinated alkane based on the total weight of the composition, preferably at least 80 wt %, more preferably at least 90 wt % based on the total weight of the composition.
12. The composition of any preceding item, wherein the composition comprises a mixture of solid thickening agents.
13. The composition of any preceding item, wherein the composition comprises 1 to 50 percent by weight, preferably 1 to 40 percent by weight, more preferably 3-40 percent by weight of the one or more solid thickening agent, based on the total weight of the composition.
14. The composition of any preceding item, wherein the solid thickening agent is comprised at a concentration of from 3 to 25 wt %, preferably from 3 to 20 wt %, more preferably from 3 to 11 wt % based on the total weight of the composition.
15. The composition of any preceding item, wherein the solid thickening agent is present at a concentration of up to 25 wt %, preferably up to 15 wt %, more preferably up to 10 wt % based on the total weight of the composition.
16. The composition of any preceding item, wherein the composition comprises 80-97 wt % of a semifluorinated alkane and 3-11 wt % of a solid thickening agent based on the total weight of the composition.
17. The composition of any preceding item, wherein the solid thickening agent is natural or synthetic.
18. The composition of any preceding item, wherein the solid thickening agent is selected from waxes, triglycerides, fatty alcohols, fatty alcohols derivatives or combinations thereof.
19. The composition of any preceding item, wherein the solid thickening agent is selected from plant waxes, animal waxes, petroleum derived waxes, triglycerides, cetyl alcohol, cetyl palmitate, tetradecanol or combinations thereof.
20. The composition of any preceding item, wherein the thickening agent is a wax selected from the group consisting of bees wax, lanolin (wool wax), carnauba wax, candelilla wax, castor wax, rice bran wax (rice wax), spermaceti wax, jojoba oil, bran wax, montan wax, kapok wax, bay berry wax, shellac wax, sugar cane wax, paraffin wax, ceresin wax.
21. The composition of any preceding item, wherein the excipient is selected from co-solvents or oily materials.
22. The composition of any preceding item, wherein the composition comprises more than one excipient.
23. The composition of any preceding item, wherein the total amount of the excipient is up to about 45 wt %, preferably up to 25 wt %, more preferably up to 10 wt %, most preferably up to 6 wt % based on the total weight of the composition.
24. The composition according to any preceding item, wherein the excipient is an oily material selected from squalane, squalene, thymol, essential oils, liquid triglycerides, emollient vegetable oils such as olive, coconut, jojoba, avocado, sunflower, safflower, borage, corn and sea buckthorn.
25. The composition according to any preceding item, wherein the co-solvent is one selected from isopropanol and ethanol, preferably isopropanol.
26. The composition of any preceding item, wherein the composition comprises 80-97 wt % of the one or more semifluorinated alkane, 3-11 wt % of a solid thickening agent and 3-6 wt % of an excipient based on the total weight of the composition.
27. The composition of any preceding item, wherein the composition is a semi-solid at room temperature that liquefies upon contact with the body of a mammal.

28. The composition of any preceding item, wherein the composition does not form a solution at room temperature.
29. The composition of any preceding item, wherein the composition presents as a creamy, homogeneous semi solid at room temperature.
30. The composition of any preceding item, wherein the composition is a lipogel.
31. The composition of any preceding item, wherein the composition is preservative-free.
32. The composition of any preceding item, comprising a) a semifluorinated alkane selected from 1-perfluohexyloctane, 1-perfluorobutyloctane or mixtures thereof, at a concentration of from 85 to 97 percent by weight; b) a solid thickening agent selected from bees wax, paraffin wax, cetyl alcohol, cetyl palmitate 15 or mixtures thereof, at a concentration of from 3 to 11 percent by weight based on the total weight of the composition.
33. The composition of item 32, further comprising an excipient selected from squalane, isopropanol, ethanol and diethyl sebacate.
34. The composition of any of items 2 to 33, wherein the active ingredient is selected from antiseptics, avermectins, prostaglandin analogues, capsaicinoids, corticosteroids, antibiotics, calcineurin inhibitors, anaesthetics, retinoids, vitamin D analogues, immunosuppressants.
35. The composition according to any of items 2 to 34, wherein the active ingredient is selected from molecular iodine, ivermectin, capsaicin, prostaglandin analogues, cyclosporin, tacrolimus, retinoids, vitamin D analogues, corticosteroids, calcineurin inhibitors.
36. The composition according to item 35, wherein the composition comprises 90-95 percent by weight of a semifluorinated alkane, 5-10 percent by weight of the one or more solid thickening agent based on the total weight of the composition, and up to about 1000 ppm molecular iodine, preferably from 250 to 1000 ppm molecular iodine.
37. The composition according to item 36, wherein the semifluorinated alkane is 1-perfluorohexyloctane and the solid thickening agent is paraffin wax.
38. The composition according to item 35, wherein the active ingredient is cyclosporin A at a concentration of from 0.1 to 0.5 percent by weight, preferably 0.1 to 0.3 percent by weight based on the total weight of the composition.
39. The composition according to item 38, wherein the solid thickening agent is Softisan® 378, preferably at a concentration of from 20 to 30 percent by weight based on the total weight of the composition, and the semifluorinated alkane is 1-perfluorohexyloctane.
40. The composition according to any of the preceding items, wherein the composition is free of water.
41. The composition of any preceding items, wherein the composition has a content of oxygen of at least 10 mg/l, preferably of at least 15 mg/l, more preferably wherein the composition is effective in transporting oxygen to the skin and has a content of oxygen of at least 10 mg/l, preferably of at least 15 mg/l.
42. The composition according to any of the preceding items for use as a medicine.
43. The composition according to item 42 for use in the prevention or treatment of a disease or condition associated with lipid barrier damage of the skin.
44. The composition for use according to item 43, wherein the disease is selected from irritant contact dermatitis, allergic contact dermatitis, atopic dermatitis, psoriasis, acne.
45. The composition for use according to item 43 to 44, wherein the condition associated with lipid barrier damage is selected from dry skin, aged skin, itchiness.
46. A kit comprising the composition as defined in any of the preceding items and a container for holding the composition.
47. A method of treating a disease or condition associated with lipid barrier damage of the skin, comprising topically administering a composition as defined in any of the items 1 to 41.
48. The method of item 47, wherein the disease is selected from irritant contact dermatitis, allergic contact dermatitis, atopic dermatitis, psoriasis, acne.
49. The method of item 47 to 48, wherein the condition associated with lipid barrier damage is selected from dry skin, aged skin, itchiness.

The present invention will be illustrated by the following examples, which are not to be understood as restricting the scope of the invention.

EXAMPLES

The ointments of Examples 1, 2 and 3 were prepared according to the following procedure: the components of the ointment were weighed and then mixed together. The mixture was gently heated in a water bath and gently shaken until a clear, homogeneous solution was obtained. Afterwards, the solution was allowed to cool down to room temperature, resulting in the formation of a semisolid composition.

The following ingredients were used: Beeswax (Acros Organics; CAS 8012-89-3) Molecular iodine (Merck; CAS 7553-56-2), Carnauba wax (Alfa Aesar; CAS 8015-86-9), Cetyl palmitate 15 (Acros Organics; CAS 540-10-3), F4H8 (Novaliq), Paraffin wax (Sigma Aldrich, CAS 8002-74-2), Squalane (Sigma Aldrich, CAS 111-01-3), F6H8 (Novaliq), Cetyl alcohol (Sigma Aldrich, CAS 36653-82-4, 99%), F4H5 (Novaliq).

The content of each component in the following compositions is expressed in percent by weight based on the total weight of the composition (wt %).

Example 1: Compositions with 2-Components

| | content in wt % | | | | | | | | | | | | | | |
|---|---|---|---|---|---|---|---|---|---|---|---|---|---|---|---|
| F6H8 | 89 | 93 | 95 | 97 | 90 | 93 | 80 | 85 | 90 | 90 | 93 | 95 | | 90 | 93 |
| F4H5 | | | | | | | | | | | | | 90 | | |
| bees wax | 11 | 7 | 5 | 3 | | | | | | | | | | | |
| carnauba wax | | | | | 10 | 7 | | | | | | | | | |
| cetyl alcohol | | | | | | | 20 | 15 | 10 | | | | | | |
| paraffin wax | | | | | | | | | | 10 | 7 | 5 | 10 | | |
| cetyl palmitate 15 | | | | | | | | | | | | | | 10 | 7 |

Example 2: Compositions with 3- or 4-Components

| | content in wt % | | | | | | | | | | |
|---|---|---|---|---|---|---|---|---|---|---|---|
| F6H8 | 93 | 90 | 90 | 90 | 90 | 90 | 90 | 90 | 88 | 90 | 90 |
| F4H5 | | | | | | | | | | | |
| bees wax | 3 | 3 | 5 | 4 | | 5 | 5 | 3 | 3 | 4 | |
| carnauba wax | | | | | | | | | | | |
| cetyl alcohol | | 7 | | | 5 | | | 4 | | 3 | |
| paraffin wax | | | | | | | | | | | |
| cetyl palmitate | 15 | 4 | | | | | | | 4 | | 5 |
| Lanolin | | | | | | 5 | | | | | |
| Vaseline | | | 5 | | | | | | | 3 | |
| Squalane | | | | 6 | 5 | | | | | | 5 |
| Isopropanol | | | | | | 5 | | 3 | 5 | | |

Example 3: Compositions Including Molecular Iodine

| F6H8 | 90 | 95 |
|---|---|---|
| paraffin wax | 10 | 5 |
| molecular iodine | 1000 ppm | 250 ppm |

Example 4 Administration

The compositions of Example 1-3 present as semi-solid compositions. When administered to the skin of the forearm, a silky feeling was recognized, with the compositions absorbing very quickly into the skin. Further, after being completely absorbed into the skin, the compositions did not leave any unpleasant greasy feeling behind. Contact of the treated skin with textiles/clothing did not lead to greasy spots.

Example 5

An ointment was prepared comprising 0.2% w/w cyclosporine A (CsA), 2% w/w EtOH, 25% w/w Softisan® 378 and 1-perfluorohexyloctane according to the following procedure: 0.10 g CsA were dissolved in 1.0 g ethanol in a glass vial; 12.50 g Softisan® 378 were weighed in a mortar and melted on a water bath at about 45° C. until a clear melt was formed. Then, the molten Softisan® 378 was left at room temperature to cool down a bit and subsequently the solution of CsA in ethanol and F6H8 were added to the molten Softisan®378, while stirring until a homogeneous semisolid formulation was formed.

The semisolid formulation appeared white and creamy, homogeneous, non-greasy and melted after spreading on the skin. Homogeneity could be confirmed by microscopic investigation, which showed no undissolved active ingredient crystals.

Example 6: Measurement of Oxygen Content in the Formulations

The general procedure for the measurement of the oxygen content in an ointment was as follows: a needle-type chemical optical oxygen microsensor (optrode or optode) was placed into a defined amount of deoxygenized olive oil (purged with N2) in a closed crimp cap vial. Then, a defined amount of a test formulation was added into the vial. After adding the formulation, the vial was closed again and gently stirred by using a magnetic stirrer. The oxygen content was measured and logged in intervals of 1 s for approx. 30 minutes.

1) Formulation A6: F6H8 90 wt %/Beeswax 4 wt %/Squalane 6 wt %
6.05 g of olive oil was purged with N2 for 10 minutes. After purging, 1.01 g of formulation A6 were added and stirred for 30 minutes using a magnetic stirrer.

2) Formulation A26: F4H8 90 wt %/Beeswax 3 wt %/Paraffin wax 3 wt %/Squalane 4 wt %
A total amount of 5.86 g of olive oil was purged with N2 for 10 min. Then 0.74 g of formulation A26 were added and stirred for 30 min using a magnetic stirrer.

3) Comparative formulation: 100% Vaseline
6.10 g of olive oil were purged with N2 for ten minutes. Then 1.20 g of Vaseline were added and stirred for 30 minutes using a magnetic stirrer.

The amount of oxygen measured reached a plateau for all formulations after about more than 25 minutes till 30 minutes. By normalizing the measured oxygen to 1 g of formulation in 6 g of olive oil, higher values of oxygen content (mg/l) were observed at about 30 minutes for both test formulations A6 (about 2.6 mg/l) and A26 (about 2.9 mg/l) compared to Vaseline (1.3 mg/l). By using the final plateau values, the following values were calculated as an estimation of the initial content of oxygen in the formulations: A6 (21 mg/L), A26 (23 mg/L), Vaseline (8 mg/L).

The invention claimed is:

1. A homogenous semi-solid composition consisting of:
   a) a semifluorinated alkane;
   b) one or more solid thickening agents; and
   c) optionally one or more excipients;
   wherein the composition is formulated for topical application to skin, and
   wherein the semifluorinated alkane is selected from 1-perfluorobutyl-pentane (F4H5), 1-perfluorobutyl-hexane (F4H6), 1-perfluorobutyl-octane (F4H8), 1-perfluorobutyl-decane (F4H10), 1-perfluorohexyl-octane (F6H8), 1-perfluorohexyl-decane (F6H10) and combinations thereof, and
   wherein the semifluorinated alkane is present at a concentration of 80-97 wt. % based on the total weight of the composition, and wherein the solid thickening agents are selected from plant waxes, animal waxes, petroleum-derived waxes, solid triglycerides, C12-24 fatty acids, C8-18 glycerides, fatty alcohols, fatty alcohol derivatives, or any combination thereof, wherein the solid thickening agents are present at a concentration of 3-11 wt % based on the total weight of the composition; and
   wherein the one or more excipients are selected from cosolvents and oily materials;
   wherein the composition is in the form of an ointment.

2. The composition of claim 1, wherein the semifluorinated alkane is selected from 1-perfluorobutyl-pentane (F4H5) and 1-perfluorohexyl-octane (F6H8).

3. The composition of claim 1, wherein the semifluorinated alkane is 1-perfluorohexyl-octane (F6H8).

4. The composition of claim 1, wherein the one or more solid thickening agents are selected from petroleum derived waxes, bees wax, paraffin wax, cetyl alcohol, cetyl palmitate, carnauba wax, lanolin, and combinations thereof.

5. The composition of claim 1, wherein the composition consists of the semifluorinated alkane, the one or more solid thickening agents, and one or more excipients selected from squalane, isopropanol, ethanol, and diethyl sebecate.

6. The composition of claim 1, wherein the composition consists of 89-97 wt. % F6H8 and 3-11 wt. % bees wax, based on the total weight of the composition.

7. The composition of claim 1, wherein the composition consists of 80-97 wt % of the semifluorinated alkane, 3-11 wt % of the thickening agent and 3-6 wt % of the one or more excipients, based on the total weight of the composition.

8. The composition of claim 1, wherein the composition is a semi-solid at room temperature that melts upon contact with the skin of a mammal's body.

9. The composition according to claim 6, wherein the composition consists of (i) 89 wt. % F6H8 and 11 wt. % bees wax, (ii) 93 wt. % F6H8 and 7 wt. % beeswax, (iii) 95 wt. % F6H8 and 5 wt. % bees wax, or (iv) 97 wt. % F6H8 and 3 wt. % beeswax, based on the total weight of the composition.

10. The composition according to claim 1, wherein the composition is a pharmaceutical composition.

11. A method for the treatment of a disease or condition associated with lipid barrier damage of skin, comprising topically administering the pharmaceutical composition of claim 10 to the skin.

12. The method according to claim 11, wherein the disease associated with the lipid barrier damage of the skin is selected from irritant contact dermatitis, allergic contact dermatitis, atopic dermatitis, psoriasis, and acne.

13. The method according to claim 11, wherein the condition associated with lipid barrier damage is selected from dry skin, aged skin, and itchiness.

14. A kit comprising the composition according to claim 1 and a container for holding the composition.

15. The composition according to claim 1, wherein the solid thickening agent is selected from bees wax, paraffin wax, cetyl alcohol, cetyl palmitate 15, and mixtures thereof.

16. The composition according to claim 1, wherein the composition consists of 88-93 wt. % F6H8 and 3-5 wt. % bees wax, based on the total weight of the composition, and one or more of cetyl palmitate 15, cetyl alcohol, squalane, and isopropanol.

17. The composition according to claim 1, wherein the composition consists of (i) 93 wt. % F6H8, 3 wt. % bees wax, and 4 wt. % cetyl palmitate 15, (ii) 90 wt. % F6H8, 3 wt. % bees wax, and 7 wt. % cetyl alcohol, (iii) 90 wt. % F6H8, 4 wt. % bees wax, and 6 wt. % squalane, (iv) 90 wt. % F6H8, 5 wt. % bees wax, 5 wt. % isopropanol, (v) 90 wt. % F6H8, 3 wt. % bees wax, 4 wt. % cetyl alcohol, and 3 wt. % isopropanol, (vi) 88 wt. % F6H8, 3 wt. % bees wax, 4 wt. % cetyl palmitate 15, and 5 wt. % isopropanol, or (vii) 90 wt. % F6H8, 5 wt % cetyl palmitate 15 and 5 wt. % squalane, based on the total weight of the composition.

18. The composition according to claim 7, wherein the composition consists of the F6H8 at a concentration of 92 percent by weight, beeswax at a concentration of 5 percent by weight and squalane at a concentration of 3 percent by weight, based on the total weight of the composition.

19. The composition according to claim 1, wherein the semifluorinated alkane is selected from 1-perfluorobutyl-pentane (F4H5) and 1-perfluorohexyl-octane (F6H8), and wherein the semifluorinated alkane is present at a concentration of 85-97 wt % based on the total weight of the composition; wherein the solid thickening agent is selected from bees wax, paraffin wax, cetyl alcohol, cetyl palmitate 15, and mixtures thereof; and wherein the solid thickening agent is present at a concentration of 3-11 wt % based on the total weight of the composition.

20. The composition of claim 1, wherein the one or more solid thickening agents are selected from plant waxes, animal waxes, petroleum-derived waxes, solid triglycerides, C8-18 glycerides, fatty alcohols, fatty alcohol derivatives, and any combinations thereof.

21. The composition of claim 1, wherein the one or more solid thickening agents are selected from plant waxes, animal waxes, petroleum derived waxes, solid triglycerides, cetyl alcohol, cetyl palmitate 15, tetradecanol, and any combinations thereof.

* * * * *